US009670131B2

(12) United States Patent
Gautam et al.

(10) Patent No.: US 9,670,131 B2
(45) Date of Patent: Jun. 6, 2017

(54) METHOD FOR PRODUCING CARBONATES

(71) Applicant: SABIC Global Technologies B.V., Bergen op Zoom (NL)

(72) Inventors: Pankaj Singh Gautam, Evansville, IN (US); William E. Hollar, Jr., Mt. Vernon, IN (US); Sergio Ferrer Nadal, Granada (ES); John Joseph Anderson, Mt. Vernon, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/111,050

(22) PCT Filed: Feb. 4, 2015

(86) PCT No.: PCT/US2015/014346
§ 371 (c)(1),
(2) Date: Jul. 12, 2016

(87) PCT Pub. No.: WO2015/119982
PCT Pub. Date: Aug. 13, 2015

(65) Prior Publication Data
US 2016/0347701 A1    Dec. 1, 2016

(30) Foreign Application Priority Data
Feb. 4, 2014   (EP) .................................... 14382038

(51) Int. Cl.
| | |
|---|---|
| *C07C 68/02* | (2006.01) |
| *B01J 19/24* | (2006.01) |
| *B01J 8/02* | (2006.01) |
| *C01B 31/28* | (2006.01) |
| *B01J 8/06* | (2006.01) |
| *B01J 8/04* | (2006.01) |
| *B01J 19/02* | (2006.01) |
| *B01J 35/00* | (2006.01) |
| *B01J 21/18* | (2006.01) |
| *B01J 27/224* | (2006.01) |
| *B01J 33/00* | (2006.01) |
| *B01J 35/06* | (2006.01) |

(52) U.S. Cl.
CPC .................. *C07C 68/02* (2013.01); *B01J 8/02* (2013.01); *B01J 8/0292* (2013.01); *B01J 8/0496* (2013.01); *B01J 8/067* (2013.01); *B01J 19/02* (2013.01); *B01J 19/2415* (2013.01); *B01J 21/18* (2013.01); *B01J 27/224* (2013.01); *B01J 33/00* (2013.01); *B01J 35/0006* (2013.01); *C01B 31/28* (2013.01); *B01J 35/06* (2013.01); *B01J 2208/0084* (2013.01); *B01J 2208/00805* (2013.01); *B01J 2219/029* (2013.01); *B01J 2219/0218* (2013.01); *B01J 2219/0236* (2013.01); *B01J 2219/0263* (2013.01); *B01J 2219/0286* (2013.01)

(58) Field of Classification Search
None
See application file for complete search history.

(56) References Cited

U.S. PATENT DOCUMENTS

| | | |
|---|---|---|
| 3,857,680 A | 12/1974 | Porta et al. |
| 4,016,190 A | 4/1977 | Bockmann et al. |
| 4,697,034 A | 9/1987 | Janatpour et al. |
| 4,792,620 A | 12/1988 | Paulik et al. |
| 5,136,077 A | 8/1992 | Rand |
| 5,167,946 A | 12/1992 | Mullins et al. |
| 5,239,105 A | 8/1993 | Pews et al. |
| 5,424,473 A | 6/1995 | Galvan et al. |
| 5,478,961 A | 12/1995 | Ooms et al. |
| 5,734,004 A | 3/1998 | Kuhling et al. |
| 5,900,501 A | 5/1999 | Ooms et al. |
| 6,054,107 A | 4/2000 | Cicha et al. |
| 6,054,612 A | 4/2000 | Cicha et al. |
| 6,348,613 B2 | 2/2002 | Miyamoto et al. |
| 6,399,823 B1 * | 6/2002 | Via .................... B01J 8/0453 502/177 |
| 6,410,678 B1 | 6/2002 | Ishida et al. |
| 6,500,984 B1 | 12/2002 | Via et al. |
| 6,531,623 B2 | 3/2003 | Chrisochoou et al. |

(Continued)

FOREIGN PATENT DOCUMENTS

| | | |
|---|---|---|
| CN | 101545579 A | 9/2009 |
| DE | 102006022629 A1 | 11/2007 |

(Continued)

OTHER PUBLICATIONS

Norskov et al.,"Towards the Computational Design of Solid Catalysts", Nature Chemistry; 2009, 1, pp. 37-46.
Albanis et al.; "Theodoros Albanis and Evcoxia Kladopoulou, Hellenic Petroleum a Heat Exchanger for Texas Tower Feed/Effluent Applications Aided the Upgrade Project of the Hellenic Petroleum Refinery at Thessaloniki"; Hydrocarbon Engineering; Feb. 2013.
English Abstract of CN 102001658 A; Date of Publication Apr. 6, 2011; 2 pages.
English Abstract of DE 19543678; Date of Publication May 28, 1997; 2 pages.

(Continued)

*Primary Examiner* — Kamal Saeed
(74) *Attorney, Agent, or Firm* — Cantor Colburn LLP

(57) ABSTRACT

In an embodiment, a method of producing carbonate can comprise: reacting a feed comprising carbon monoxide and chlorine in a tube of a reactor to produce a product composition comprising phosgene, wherein the tube has a particulate catalyst contained therein, wherein a thermally conductive material separate from the tube contacts at least a portion of the particulate catalyst, and wherein carbon tetrachloride is present in the product composition in an amount of 0 to 10 ppm by volume based on the volume of the phosgene; and reacting a monohydroxy compound with the phosgene to produce the carbonate.

20 Claims, 1 Drawing Sheet

(56) References Cited

U.S. PATENT DOCUMENTS

| | | |
|---|---|---|
| 6,548,691 B2 | 4/2003 | Alewelt et al. |
| 6,680,400 B2 | 1/2004 | Alewelt et al. |
| 6,930,202 B1 | 8/2005 | Heuser et al. |
| 7,442,835 B2 | 10/2008 | Keggenhoff et al. |
| 7,771,674 B2 | 8/2010 | Suzuta et al. |
| 7,812,189 B2 | 10/2010 | Fukuoka et al. |
| 8,044,226 B2 | 10/2011 | Fukuoka et al. |
| 8,409,539 B2 | 4/2013 | Olbert et al. |
| 8,518,231 B2 | 8/2013 | Ooms et al. |
| 8,993,803 B2 | 3/2015 | Olbert et al. |
| 9,175,135 B2 | 11/2015 | Ooms et al. |
| 2002/0065432 A1 | 5/2002 | Eckert et al. |
| 2005/0014965 A1 | 1/2005 | Dahlmann et al. |
| 2009/0143619 A1 | 6/2009 | Kauth et al. |
| 2016/0176715 A1 | 6/2016 | Gautam et al. |
| 2016/0207779 A1 | 7/2016 | Gautam et al. |

FOREIGN PATENT DOCUMENTS

| | | |
|---|---|---|
| EP | 0251586 A2 | 1/1988 |
| EP | 0633241 A1 | 1/1995 |
| EP | 0722931 A1 | 7/1996 |
| EP | 0796819 A1 | 9/1997 |
| EP | 0936184 A2 | 8/1999 |
| EP | 1033167 A2 | 9/2000 |
| EP | 1112997 A2 | 7/2001 |
| EP | 1234845 A2 | 8/2002 |
| EP | 1633172 A2 | 3/2006 |
| EP | 1783112 A1 | 5/2007 |
| EP | 1651565 B1 | 8/2011 |
| FR | 2003931 A1 | 11/1969 |
| WO | 9730932 | 8/1997 |
| WO | 2012076532 A1 | 6/2012 |
| WO | 2015119981 A2 | 8/2015 |

OTHER PUBLICATIONS

English Abstract of EP 0483632; Date of Publication May 6, 1992; 1 page.

English Abstract of JP 4785515 B2; Date of Publication Oct. 5, 2011; 2 pages.

English Abstract of JP 6029129 A; Date of Publication Feb. 4, 1994; 2 pages.

English Abstract of JP 6340408 A; Date of Publication Dec. 13, 1994; 2 pages.

English Abstract of JP 9059012 A; Date of Publication Mar. 4, 1997; 2 pages.

European Search Report for European Application No. 14382038.9; Date of Completion: Jul. 9, 2014; 5 pages.

International Search Report for International Application No. PCT/US2015/014346; International Filing Date Feb. 4, 2015; Date of Mailing Oct. 29, 2015; 4 pages.

Naphon et al.; "A review of flow and heat transfer characteristics in curved tubes"; Renewalbe and Sustainable Energy Reviews; 10 (2006); pp. 463-490.

Written Opinion of the International Search Report for International Application No. PCT/US2015/014346; International Filing Date Feb. 4, 2015; Date of Mailing Oct. 29, 2015; 5 pages.

* cited by examiner

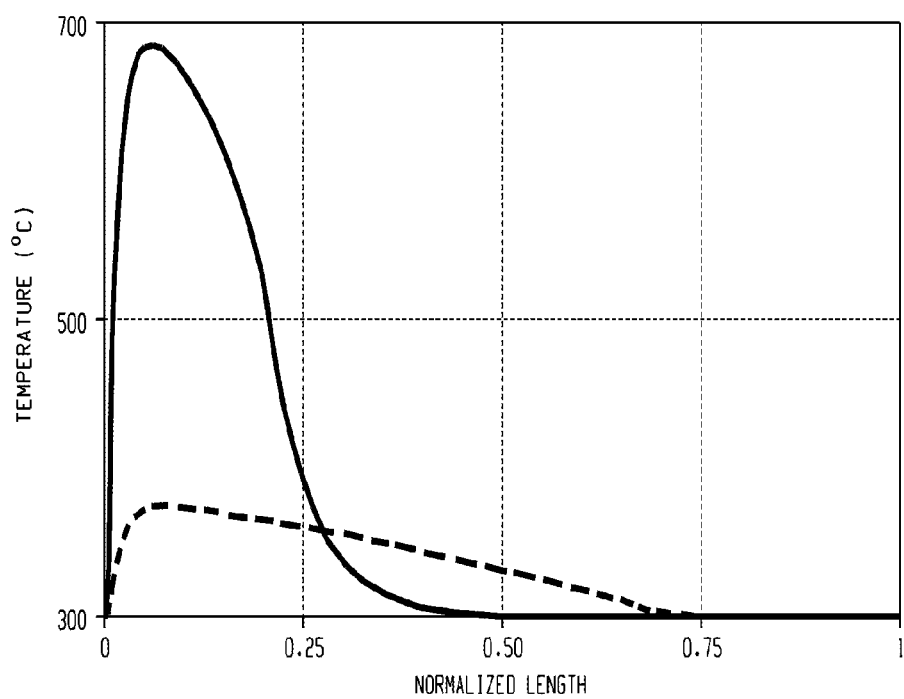

METHOD FOR PRODUCING CARBONATES

CROSS REFERENCE TO RELATED APPLICATIONS

This application is a National Stage application of PCT/US2015/014346, filed Feb. 4, 2015, which claims the benefit of EP Application No. 14382038.9, filed Feb. 4, 2014, both of which are incorporated by reference in their entirety herein.

BACKGROUND

Diaryl carbonates have been used for the production of polycarbonates. The production of diaryl carbonates can proceed by production of phosgene and subsequent reaction of phosgene with monophenols. However, phosgene used for the production of diaryl carbonates may contain impurities such as carbon tetrachloride that results in the formation of organic chlorides as impurities in the produced diaryl carbonates, particularly diphenyl carbonate. Diphenyl carbonates containing high levels of organic chlorides are unsuitable for use in polycarbonate synthesis as they adversely impact the polymerization reaction and may also result in adverse color. Thus there is a strong incentive to use phosgene having low levels of organic chloride compounds for the synthesis of diaryl carbonates in general and diphenyl carbonate in particular.

In one method for producing phosgene, carbon monoxide is reacted with chlorine in the presence of a carbon-comprising catalyst such as activated carbon or silicon carbide. The reaction is strongly exothermic and is usually performed in a reactor such as a multi-tubular reactor that has been designed similarly to conventional shell and tube heat exchangers.

A carbon tetrachloride by-product can result from the phosgene reaction and can be present in an amount of 50 to 300 parts per million (ppm) by volume or higher. Carbon tetrachloride can be formed in the phosgene reaction via multiple reaction routes one of which involves the direct chlorination of catalyst carbon. The presence of high levels of carbon tetrachloride in phosgene as an impurity can be disadvantageous in the production of diaryl carbonates. Presence of high amounts of carbon tetrachloride leads to an increase of organic impurities in the diaryl carbonate which might cause a reduction of the catalytic activity in the polymerization reaction as well as discoloration issues in the final polycarbonate resin. According to U.S. Pat. No. 8,044,226, 1 ppm of chlorinated impurities is sufficient to inhibit the polymerization reaction, whereas less than 1 ppb is preferably in order to synthesize an uncolored polycarbonate with perfect transparency.

Current processes for the purification of diphenol carbonate are mostly based on a cascade of distillation columns. For example, U.S. Pat. No, 5,734,004 discloses a purification method based on distillation in which diphenol carbonate is removed in vapor phase from a side-draw. U.S. Pat. Nos. 5,734,004, 7,812,189 describes a purification method in which diphenol carbonate is also obtained as a side-draw in vapor phase. U.S. Pat. No. 7,812,189 discloses that the purification method is able to produce a high-purity diphenol carbonate with less than 1 ppb of chlorides. WO2012/076553 discloses the purification of diphenol carbonate from chlorides, metals and other heavy contaminants by using a non-porous membrane or nanofiltration membrane with a pore size up to 10 nm. EP0722931A1 discloses a method to prepare a high-purity diphenyl carbonate free of chlorinated impurities by distillation in the presence of abasic substance.

However, phosgene purification to remove carbon tetrachloride can be difficult and is a significant part of capital investment and operating costs of any phosgene plant due to the costly material of construction of the purification equipment, the need for large enclosures to house said equipment, and further because the process is very energy intensive. On a global basis, the amount of byproduct carbon tetrachloride produced in commercial phosgene manufacturing annually can be as much as 2 million kilograms based on phosgene production of about 4 billion kilograms.

A method to produce diaryl carbonates without the need for a separate phosgene purification process is therefore desirable.

BRIEF SUMMARY

Disclosed is a method of producing carbonate, such as diaryl carbonate, dialkyl carbonate, and polycarbonate.

In an embodiment, a method of producing carbonate can comprise: reacting a feed comprising carbon monoxide and chlorine in a tube of the reactor to produce a product composition comprising phosgene, wherein the tube has a particulate catalyst contained therein, wherein a thermally conductive material separate from the tube contacts at least a portion of the particulate catalyst, and wherein carbon tetrachloride is present in the product composition in an amount of 0 to 10 ppm by volume based on the volume of the phosgene; and reacting a monohydroxy compound with the phosgene to produce the carbonate.

The above described and other features are exemplified by the following Detailed Description, Figure, and Examples.

BRIEF DESCRIPTION OF THE DRAWING

FIG. 1 is a graphical illustration of temperature versus normalized length in a lab scale tube and an industrial scale tube according to U.S. Pat. No. 6,399,823.

DETAILED DESCRIPTION

Phosgene is typically produced in packed bed multi-tubular reactors. A typical multi-tubular reactor for use as a phosgene reactor consists of a shell housing a number of tubes packed with a catalyst and a cooling medium circulating between the tubes and the shell to remove the heat of the reaction. Because typical catalysts have poor thermal conductivity and the multi-tubular design of the reactor is limited in terms of effective heat transfer area, the reactor can have high peak tube temperatures (hot spots) in the range of 400 to 800 degrees Celsius (° C.). It was surprisingly found that the formation of carbon tetrachloride is directly related to the peak reaction temperature in the packed bed, and without being bound by theory, it is believed that the formation of carbon tetrachloride primarily occurs in these hot spots. The Applicants therefore developed a novel phosgene reactor that results in a reduced amount of carbon tetrachloride production and that can be used on an industrial scale. For example, the phosgene reaction can produce greater than or equal to 2,000 kilograms per hour (kg/hr), specifically, greater than or equal to 4,000 k/hr, more specifically, 4,000 to 13,000 kg/hr or 4,000 to 9,000 kg/hr of product.

U.S. Pat. No. 6,500,984 discloses synthesis of high purity phosgene containing less than 10 ppmv carbon tetrachloride as an impurity in a packed bed tubular reactor comprising a composite catalyst bed, where the relative activity towards phosgene of a second catalyst bed located at the outlet end of the composite reactor is higher than that of a first catalyst bed located at the inlet end. U.S. Pat. No. 6,500,984 discloses that the use of composite catalyst beds can lower the amount of carbon tetrachloride formed in phosgene synthesis by about 2 at low temperature and about 5 times lower at high temperature in comparison with the uniform catalyst bed of high activity alone. A packed tube having an outside diameter of 0.5" fitted with a moving thermocouple in an axial slide tube (0.125" diameter) was employed to demonstrate proof of concept.

The Applicants found that the composite bed configuration of U.S. Pat. No. 6,500,984 did not scale-up well for use in the industrial production of phosgene as industrial scale reactors, see Examples below. They discovered that when the composite catalyst bed of U.S. Pat. No. 6,500,984 was applied to a typical industrial scale reactor tube with a 2 inch diameter and a length of 8 feet and operating under equivalent conditions of U.S. Pat. No. 6,500,984 (reactant ratio, flow velocity, inlet temperature, etc.) that the phosgene produced had a significantly higher phosgene level as was disclosed in U.S. Pat. No. 6,500,984.

Without being bound by theory, the Applicants believe that the composite catalyst bed of U.S. Pat. No. 6,500,984 does not scale up because the time scale of heat removal in packed beds becomes progressively larger. In other words, it is believed that heat removal becomes less efficient with the increase in tube diameter. A characteristic heat removal time can be defined as follows:

$$\tau = \frac{C_{pv}V_r}{UA_h}$$

where $C_{pv}$ is the volumetric specific heat of the reaction mixture, $V_r$ is the reactor volume, $A_h$ is the heat transfer area, and U is the overall heat transfer coefficient for the catalyst bed. As the characteristic rate of heat removal is proportional to the inverse of the characteristic time, it is clear that the rate of heat removal varies inversely with the tube diameter. Therefore, it is clear that as the tube diameter increase from 0.5 inches to 2 inches, the catalyst bed becomes less efficient at removing the heat of the reaction. This decrease in heat removal efficiency results in a higher peak tube temperature profile with a greater likelihood of hot spot formation.

The Applicants further found that higher peak tube temperatures are linked to increased formation of carbon tetrachloride. Specifically, using a lab scale packed bed phosgene reactor, the Applicants found that peak tube temperature is correlated with formation of carbon tetrachloride through the following equation:

$$\ln(CCl4)(ppm)=0.0049*T_{max}(K)-1.817$$

Thus higher peak tube temperatures in a 2 inch industrial scale reactor as compared with a 0.5 inch lab scale tube reactor result in significantly higher carbon tetrachloride formation even when a composite catalyst bed is used.

Accordingly, the Applicants developed a novel reactor design that can be used in the industrial scale production of phosgene that results in a lower characteristic heat removal time and thus achieves significantly lower carbon tetrachloride in phosgene. This reactor configuration comprises increasing the available heat transfer area per unit reactor volume by using a) internally finned reactors having extended internal surface area and/or inserts that can provide higher effective heat transfer area per unit reactor volume, b) use of high heat conductivity inert fillers in the catalyst bed, c) catalyst modification to improve pellet heat conductivity, and d) tube designs with extended external surface area through finned tubes to improve external heat transfer to the cooling medium, e) inducing greater turbulence in flow internally or externally to the tube for improved overall heat transfer, and f) a combination comprising one or more of the foregoing.

It was therefore surprisingly found that reducing or eliminating the formation of hot spots in the phosgene reactor such that the peak reaction temperature is less than 800° C., for example, equal to or less than 400° C., specifically, less than or equal to 350° C., more specifically, less than or equal to 300° C. could result in the formation of phosgene with less than or equal to 10 ppm, less than or equal to 9 ppm, less than or equal to 8 ppm, less than or equal to 7 ppm, less than or equal to 6 ppm, less than or equal to 5 ppm, less than or equal to 4 ppm, less than or equal to 3 ppm, less than or equal to 2 ppm, less than or equal to 1 ppm, or 0 ppm, by volume of carbon tetrachloride. The Applicants have therefore developed a process and a reactor that could reduce or prevent formation of hot spots by increasing available heat transfer area per unit volume of the reactor. For example, a typical commercial multi-tubular phosgene reactor has an effective heat transfer area per unit volume of the order of 100 square meters per cubic meters ($m^2/m^3$). Use of a modified reactor design to increase wall contact area per unit volume to increase bed-to-reactor wall heat transfer is illustrated in the various embodiments described below. It was surprisingly found that by replacing or modifying such multi-tubular reactors with a reactor configuration that better facilitates heat removal, the concentration of carbon tetrachloride can be reduced. The reactor can be a tube reactor having a heat transfer area per unit volume of 100 to 10,000 $m^2/m^3$, 500 to 8,000 $m^2/m^3$, 500 to 5,000 $m^2/m^3$, or 1,000 to 5,000 $m^2/m^3$.

To achieve these results, a tube that contains the catalyst is modified to provide improved thermal conduction away from the catalyst. In particular, a thermally conductive material separate from the tube contacts at least a portion of the particulate catalyst. In other words, a conductive material that is not a wall or other component of a convention tube contacts the particulate catalyst to improve thermal conduction away from the catalyst or to increase the thermal conductivity of the catalyst itself.

The thermally conductive material can contact at least a portion of an exterior of the particulate catalyst. The thermally conductive material can provide a thermally conductive path between the particulate catalyst and the tube. The path can be continuous or broken. A plurality of continuous paths can be present.

For example, the thermally conductive material can be a coating disposed on at least a portion of an exterior surface of the particulate catalyst, i.e., on at least a portion of the catalyst particles or on at least a portion of the exterior surface of agglomerates of the catalyst particles, or both. As used herein, "exterior surface" of the particulate catalyst does not include the pore openings, or the surfaces of the pores themselves. Contact between the thermally conductive coating on the exterior surfaces of the catalyst particles or agglomerates of the catalyst particles can provide a thermally conductive pathway from the particles or agglomerates and the tube. Even where the path is not continuous to the tube wall, such inter-particle or inter-agglomerate contact can better dissipate heat within the catalyst bed and thus decrease or prevent hot spots in the bed.

The coating can be continuous or discontinuous over the exterior surfaces. The thermally conductive coating can have a coating thickness of 0.001 to 1 micrometer, specifically, 0.01 to 0.1 micrometer, depending on the material used and the desired level of conductivity. The coating thickness can be uniform or can vary. Methods for the deposition of such coatings can be, for example, chemical vapor deposition, thermal spraying, dip coating, or powder coating. The particular method is selected in part to decrease, minimize, or prevent substantial blocking of the catalyst pore openings or coating of the pore surfaces. It is to be understood that some blocking of the catalyst pore openings or coating of the pore surfaces can occur without significantly adversely affecting the activity of the catalyst.

A plurality of continuous paths can be provided by a thermally conductive, 3-dimensional mesh disposed within a packed catalyst bed and contacting at least a portion of the exterior surfaces of the catalyst particles or agglomerates. The mesh openings can have any configuration (round, oval, square, rectangular, or the like) and the size of the openings can be selected to provide the desired degree of contact and thermal conductivity. The mesh can be regular, for example woven, or irregular, for example a nonwoven felt. Generally the openings can have an average diameter larger than the average diameter of the particulate catalyst.

A plurality of continuous, thermally conductive paths can be provided by intermixing a thermally conductive particulate material with the particulate catalyst. The thermally conductive particulate material and the particulate catalyst can be disposed in the reactor as a packed bed, or disposed on a wall of the reactor. The thermally conductive particulate material can be of any shape, including irregular or regular, e.g., spherical, oval, and the like, and of any size, although the average diameter will often be within ±20% or ±10% of the catalyst particles or agglomerates of catalyst particles. In an embodiment, the shape and size are selected to provide close packing with the particulate catalyst. The thermally conductive particulate material can be randomly distributed or distributed in a pattern. Even where the thermally conductive particulate material does not provide a continuous path to a surface of the tube, it can function to spread heat within the bed and thus decrease, minimize, or eliminate hot spots in the reactor, for example, as compared to beds that do not employ the thermally conductive particulate material.

A sheet of a thermally conductive mesh can be placed in the packed bed or over the wall to maintain the thermally conductive particles in place, where the average diameter of the openings of the mesh are smaller than the average diameter of the thermally conductive particulate material. Alternatively, a thermally conductive, 3-dimensional mesh as described above can be disposed within a packed catalyst bed containing the particulate thermally conductive material and the particulate catalyst to provide thermally conductive paths.

Another method to increase the thermal conductivity of the catalyst is to increase the level of thermally conductive materials within the catalyst itself. Carbon catalysts, for example, can inherently contain one or more thermally conductive materials in a total amount 1,000 ppm or less by weight of the catalyst. Increasing the level of thermally conductive materials to 10,000 ppm or more by weight, or 100,000 ppm or more by weight can increase contact between a thermally conductive material and the catalyst, and thereby increase the thermal conductivity of the catalyst. The amount of doped thermally conductive materials is preferably below a level that significantly adversely affects catalyst activity or product purity. Even where the presence of doped thermally conductive materials do not provide a continuous path to a surface of the tube, it can function to spread heat within the catalyst bed and thus decrease, minimize, or eliminate hot spots in the reactor.

Any combination of the above-described methods can be used, for example a combination of coated particulate catalyst, and particulate thermally conductive material, optionally together with a thermally conductive doped catalyst.

A wide variety of thermally conductive materials can be used having a thermal conductivity greater than 2 Watts per meter per degree Kelvin (W/(m·K)), greater than 15 W/(m·K), greater than 50 W/(m·K), or greater than 100 W/(m·K). The thermally conductive material can have a thermal conductivity greater than 200 W/(m·K). Examples of such thermally conductive materials include aluminum, aluminum brass, aluminum oxide, antimony, beryllium, beryllium oxide, brass, bronze, cadmium, carbon nanotubes, graphene, carbon steel, copper, gold, iridium, iron, lead, magnesium, molybdenum, nickel, silver, steel, stainless steel, and Chrome Nickel Steel (18wt % Cr, 8wt % Ni), or a combination comprising at least one of the foregoing can be used, including an alloy of the various metals. The thermally conductive material is further selected so as to not significantly adversely affect catalyst activity, reactor functioning, product yield, or product purity.

The foregoing methods are readily adapted for use in multi-tubular reactors, which can comprise any number of tubes as is known in the art, for example, 1 to 1,200, specifically, 2 to 250, more specifically, 3 to 200, seven more specifically, 1 to 200, yet more specifically, 1 to 150 or 1 to 100 inner tubes located within an outer tube, often referred to as a "shell." A cooling medium can be located between the shell and the microtube.

Each tube independently can have an average cross-sectional diameter of greater than or equal to 6 millimeters (mm), for example, greater than or equal to 8 mm, specifically, greater than or equal to 10 mm, more specifically, greater than or equal to 12 mm. Each tube independently can have an average cross-sectional diameter of greater than or equal to 20 mm, specifically, greater than or equal to 40 mm, more specifically, greater than or equal to 80 mm, or higher, for example, depending on the throughput of the reaction. Each tube independently can have an average diameter of less than or equal to 500 mm, for example, less than or equal to 250 mm, specifically, less than or equal to 100 mm, more specifically, less than or equal to 50 mm. The cross-sectional shape of the channels can be rectangular, square, round, ovoid, elliptical, or any other regular or irregular geometry. When the shape is not round, the "average microtube channel cross-sectional diameter" refers to the diameter of a circle having the same area as the actual cross-sectional shape.

The location of the catalyst in the reactor can further significantly affect the heat transfer from the reaction to the cooling liquid. Specifically, the catalyst can be deposited on (i.e., can be in direct contact with) a wall of reactor tube. In an embodiment, the deposited catalyst is used in combination with a packed bed. However, better heat transfer can be obtained where the deposited catalyst is the only catalyst used in the reaction to produce phosgene. The fact that the catalyst can be deposited on a tube or channel wall instead of being packed within the tubes or channels can result in a reduction in plugging. Without being bound by theory, it is believed that the deposited catalyst can facilitate heat removal from the reactor because the catalyst particles are in direct contact with the reactor wall rather than primarily in contact with each other. Deposited catalyst can be used in any of the above reactor and tube configurations.

Accordingly, a tube reactor can comprise a shell and a tube located within the shell, with a cooling medium between the shell and the tube, the tube having a particulate catalyst effective to convert carbon monoxide and chlorine to phosgene disposed therein, wherein a thermally conductive material separate from the tube contacts at least a portion of the particulate catalyst, and can optionally provide a thermally conductive path between the particulate catalyst and the tube. The thermally conductive material can have a thermal conductivity of greater than 2 W/(m·K), or greater than 15 W/(m·K), or greater than 100 W/(m·K), or greater than 200 W/(m·K). It can be a coating disposed on at least a portion of an exterior surface of the catalyst particles, or a portion of an exterior surface of agglomerates of the catalyst particles, or both, and can have a coating thickness of 0.001 to 1 micrometer, and the coating can be deposited by chemical vapor deposition, thermal spraying, dip coating, or powder coating. Alternatively, or in addition, the thermally conductive particulate material can be a thermally conductive, 3-dimensional mesh, optionally wherein the openings of the mesh have an average diameter larger than the average diameter of agglomerates of the particulate catalyst; or the thermally conductive material can be a particulate material distributed within and in contact with the particular catalyst, optionally wherein the thermally conductive particulate material and the particulate catalyst are further contacted by a mesh disposed within the tube. The thermally conductive material can be doped in the catalyst in an amount of greater than or equal to 10,000 ppm by weight of the catalyst, or greater than or equal to 100,000 ppm by weight of the catalyst.

A variety of different catalysts that facilitate the reaction between carbon monoxide and chlorine can be used in the above-described methods and reactors. The catalyst can be a carbon-comprising catalyst such as activated charcoal. The carbon can be from, for example, wood, peat, coal, coconut shells, bones, lignite, petroleum-based residues, sugar, and the like, or a combination comprising one or more of the foregoing. The carbon catalyst can be in particulate forms such as powder, granules, pellets, and the like, or a combination comprising one or more of the foregoing. The carbon surface area as determined by Brunauer—Emmett—Teller (BET) measurement can be greater than or equal to 100 square meters per gram ($m^2/g$), specifically, greater than or equal to 300 $m^2/g$, more specifically, greater than or equal to 1,000 $m^2/g$. The carbon surface area as determined by BET measurement can be 100 to 2,000 $m^2/g$, specifically, 550 to 1,000 $m^2/g$. Examples of commercially available carbon catalysts include Barnebey Sutcliffe™, Darco™, Nuchar™, Columbia JXN™, Columbia LCK™, Calgon PCB™, Calgon BPL™, Westvaco™, Norit™, and Barnebey Cheny NB™.

The catalyst can be an oxidatively stable catalyst. "Oxidatively stable" means that the catalyst loses less than or equal to 12wt % when sequentially heated in air for the following times and temperatures: 125° C. for 30 minutes, 200° C. for 30 minutes, 300° C. for 30 minutes, 350° C. for 45 minutes, 400° C. for 45 minutes, 450° C. for 45 minutes, and finally at 500° C. for 30 minutes. This sequence of time and temperature conditions for evaluating the effect of heating carbon samples in air can be run using thermal gravimetric analysis (TGA).

The catalyst can comprise an active metal content of less than or equal to 1,000 ppm by weight. The active metal can comprise one or more of a transition metal of Groups 3 to 10 of the Periodic Table, boron, aluminum, silicon, or a combination comprising one or more of the foregoing. The catalyst can be free of iron, where free of iron can mean that the catalyst comprises less than or equal to 100 ppm by weight, specifically, 0 to 50 ppm by weight of iron. Likewise, the catalyst can comprise less than or equal to 200 ppm by weight, specifically, less than or equal to 100 ppm by weight of sulfur and/or less than or equal to 200 ppm by weight, specifically, less than or equal to 100 ppm by weight of phosphorus. Carbon catalysts that comprise less than or equal to 1,000 ppm of active metals can be obtained by acid washing (for example, carbons that have been treated with hydrochloric acid or hydrochloric acid followed by hydrofluoric acid).

The catalyst can be a composite carbon comprising a porous carbonaceous material with a three dimensional matrix obtained by introducing gaseous or vaporous carbon-containing compounds (for example, hydrocarbons) into a mass of granules of a carbonaceous material (for example, carbon black); decomposing the carbon-containing compounds to deposit carbon on the surface of the granules; and treating the resulting material with an activator gas comprising steam to provide the porous carbonaceous material. A carbon-carbon composite material is thus formed, which is suitable as a catalyst. Such porous carbon-carbon composites can have a surface area as determined by BET measurement of greater than or equal to 10 $m^2/g$, and can include (1) a micropore to macropore ratio of less than or equal to 3.5, specifically, less than or equal to 2.0, more specifically, less than or equal to 1.0, even more specifically, 0 to 1.0; and (2) a loss of less than or equal to 16% of its weight, specifically, less than or equal to 10% of its weight, more specifically, less than or equal to 5% of its weight when sequentially heated in air for the following times and temperatures: 125° C. for 30 minutes, 200° C. for 30 minutes, 300° C. for 30 minutes, 350° C. for 45 minutes, 400° C. for 45 minutes, 450° C. for 45 minutes, and finally at 500° C. for 30 minutes. Such a catalyst can comprise an active metal content greater than or equal to 1,000 ppm. The sequence of time and temperature conditions for evaluating the effect of heating carbon samples in air can be run using TGA. The term "micropore" means a pore size of less than or equal to 20 angstroms (Å) and the term "macropore" means a pore size of greater than 20 Å. The total pore volume and the pore volume distribution can be determined, for example, by methods such as porosimetry. The micropore volume (centimeters cubed per gram (cc/g)) can be subtracted from the total pore volume (cc/g) to determine the macropore volume. The ratio of micropores to macropores can then be calculated. Examples of commercially available porous carbons include Calgon X-BCP™ and Calsicat™.

The catalyst can comprise a silicon carbide catalyst. The silicon carbide catalyst can have a surface area as determined by BET measurement of greater than or equal to 10 square meters per gram ($m^2/g$), specifically, greater than or equal to 20 $m^2/g$, more specifically, greater than or equal to 100 $m^2/g$, more specifically, greater than or equal to 300 $m^2/g$. The silicon content can be less than or equal to 10 wt %, specifically, less than or equal to 5 wt %. The silicon carbide catalyst can be manufactured using, for example, a process that comprises contacting silicon monoxide with finely divided carbon (such as one comprising an ash content of less than or equal to 0.1 wt %) or by reacting vapors of silicon monoxide (SiO) with carbon.

Each tube of the reactor can comprise one or more catalyst zones. As described briefly above, when the catalyst is deposited on a surface of a tube, the tube can comprise a first catalyst zone located at or toward the feed end that comprises less catalyst. The tube can further comprise a second catalyst zone located at or toward the outlet end that can comprise the same or different catalyst, at a higher concentration than the first catalyst. The thermally conductive material can be located in the first catalyst zone and/or the second catalyst zone. The two catalyst zones can be sequentially located. Alternatively, the deposition can be gradually increased so that catalyst concentration forms a smooth (for example, a linear or a non-linear gradient) or step gradient along each catalyst zone, with the lower activity being present at the beginning of the first catalyst zone and the higher activity being located at the second catalyst zone.

Alternatively, or in addition, a combination of lower activity catalyst and higher activity catalyst in the packed bed can be used, as described in U.S. Pat. No. 6,500,984. For example, the reactor can comprise a first catalyst zone located at or toward the feed end that comprises a first catalyst having a first activity. The reactor can further comprise a second catalyst zone located at or toward the outlet end that can comprise the same or different catalyst, having a second activity higher than the activity of the first catalyst. The two catalyst zones can be sequentially located. Alternatively, at least a portion of the first catalyst can be intermixed with the second catalyst, such that the activity of the catalyst forms a smooth or step gradient along each catalyst zone, with the lower activity being present at the beginning of the first catalyst zone and the higher activity being located at the second catalyst zone.

As described in KR1998700231A, the reactor can comprise a first catalyst zone located in the feed end that comprises a catalyst diluted with an inert filler that does not itself react under the reaction conditions and that does not catalyze or otherwise inhibit the phosgene synthesis reaction. The reactor can further comprise a second catalyst zone located at the outlet end that can comprise the same or different catalyst, which is diluted with less inert filler than in the first catalyst zone. Likewise, the reactor can comprise a first catalyst zone that contains catalyst diluted with an inert filler and a second catalyst zone that contains the same or different catalyst that is not diluted with inert filler. The inert filler can be evenly distributed among catalyst particles and the two catalyst zones can be sequentially loaded with catalyst containing inert filler in a first catalyst zone followed by catalyst in a second catalyst zone containing less inert filler. Alternatively, inert filler can be distributed in a gradient among catalyst particles in each catalyst zone with the highest concentration of inert filler being present at the beginning of a first catalyst zone and the concentration of inert filler gradually decreasing until the lowest concentration of inert filler is attained at an end of a second catalyst zone. The inert filler can be distributed in a gradient among catalyst particles in a first catalyst zone with the highest concentration of inert filler being present at the beginning of a first catalyst zone and the concentration of inert filler gradually decreasing until the lowest concentration of inert filler is attained at an end of a first catalyst zone, and the second catalyst zone contains no inert filler. A proportion of catalyst near the outlet or exit point of product gases from a catalyst bed can be undiluted with inert filler, while any remaining portion of catalyst nearer the initial point of contact of catalyst with reactant gases can be diluted with inert filler. Those skilled in the art will realize that the distribution of any filler in any catalyst zone can be homogeneous or in a gradient or somewhere in-between, for example in a step gradient.

The inert filler can comprise a low porosity material, such as a ceramic, graphite, glassy carbon, glass, quartz, a metal, or a combination comprising one or more of the foregoing. The material can have a porosity of less than or equal to 0.8 pore volume per volume of material (vol/vol), specifically, less than or equal to 0.6 vol/vol, more specifically, 0.1 to 0.5 vol/vol, for example, 0.4 vol/vol. Suitable metals comprise those that are not reactive under the reaction conditions and more specifically that are not reactive toward chlorine, carbon monoxide, or phosgene under the reaction conditions. For example, inert metal fillers can comprise stainless steel; titanium; nickel; metal alloys, including, but not limited to, nickel alloys comprising iron and chromium (such as INCONEL™), or nickel alloys comprising molybdenum and chromium (such as HASTELLOY™); or a combination comprising one or more of the foregoing. Suitable inert fillers are at least substantially inert in that they do not themselves react at an appreciable rate under the reaction conditions and do not catalyze or otherwise inhibit the phosgene synthesis reaction. Substantially inert in the present context means that a filler does not produce a level of byproducts that is outside a specification range for phosgene product.

The carbon monoxide and the chlorine gas used to prepare the phosgene can be high purity grades. The carbon monoxide can be supplied from an on-site generating plant and can comprise trace amounts of impurities such as hydrogen, methane, volatile sulfur compounds, and nitrogen. Recycled carbon monoxide recovered from a phosgene product stream can also be employed as part of the carbon monoxide-comprising feed stream.

The carbon monoxide and the chlorine can be introduced to the reactor in an equimolar amount or in a molar excess of chlorine. For example, the molar ratio of carbon monoxide to chlorine can be 1.00:1 to 1.25:1, specifically, 1.01 to 1.20:1, more specifically 1.01:1 to 1.21:1, even more specifically, 1.02:1 to 1.12:1, still more specifically, 1.02:1 to 1.06:1.

The initial feed to the reactor can comprise all of the carbon monoxide and all of the chlorine reactants Likewise, all of the chlorine can be added, where a first amount of carbon monoxide can be introduced to a first stage reaction zone and a second amount of carbon monoxide can be introduced to at least one downstream reaction zone. At least one downstream reaction zone can be in serial communicating relationship with the first reaction zone and the initial molar ratio of carbon monoxide to chlorine can be less than one, specifically, 0.999:1 to 0.2:1, more specifically, 0.999:1 to 0.5:1, even more specifically 0.999:1 to 0.8:1, more specifically, 0.999:1 to 0.95:1 more specifically, 0.999:1 to 0.98:1.

The reactor can comprise a corrosion resistant material or can be lined with a corrosion resistant material. A corrosion resistant material is one which is essentially inert to chlorine, carbon monoxide, and phosgene (such as ceramic, stainless steel, titanium, nickel, or metal alloys, including, but not limited to, nickel alloys comprising iron and chromium (such as INCONEL), or nickel alloys comprising molybdenum and chromium (such as HASTELLOY)).

The phosgene produced by this method can be used in a variety of industrial processes, for example, the manufacture of diaryl carbonates, dialkyl carbonates, polycarbonates, and the like.

A method of producing a diaryl carbonate comprises reacting an aromatic monohydroxy compound with phosgene produced according to the methods disclosed herein. Phosgene can be used in the liquid state, gaseous state or in an inert solvent.

Aromatic monohydroxy compounds include $C_{6-12}$ aromatic monohydroxy compounds which can be unsubstituted or substituted with 1 to 3 halogen, $C_{1-6}$ alkoxy, cyano, $C_{1-6}$ alkoxycarbonyl, $C_{6-12}$ aryloxycarbonyl, $C_{1-6}$ acyloxy, or nitro groups, provided that the valence of any substituted carbon is not exceeded. Examples include phenol, o-, m- or p-cresol, o-, m- or p-chlorophenol, o-, m- or p-bromophenol, 2,4-dichlorophenol, 2,4,6-tribromophenol, o-, m- or p-methoxyphenol, 2,6-dimethylphenol, 2,4-dimethylphenol, 3,4-dimethylphenol, p-tert-butylphenol, p-cumylphenol, p-n-octylphenol, p-isooctylphenol, p-n-nonylphenol, p-isononylphenol, 1-naphthol, 2-naphthol, and methyl salicylate. Phenol can be specifically mentioned.

The reaction between phosgene and aromatic monohydroxy compounds is known and has been described, for example, in U.S. Pat. Nos. 4,016,190, 4,697,034, 5,167,946, 5,424,473, 5,900,501, 6,348,613, and 8,518,231.

The reaction conditions are not particularly limited and include those that have been disclosed in the art. In an exemplary process, the reaction of phosgene and the aromatic monohydroxy compound is conducted in a phase boundary process, in which, phosgene is reacted with the aromatic monohydroxy compound in the presence of a base and optionally a basic catalyst.

Bases for the reaction of the aromatic monohydroxy compound with phosgene are, for example, alkali metal hydroxides, such as, Na, K and/or Li hydroxide. Sodium hydroxide solution is specifically mentioned. The base can be used as 10 to 25% strength by weight aqueous solution.

The basic catalyst used can be open-chain or cyclic, and include tertiary amines, N-alkylpiperidines, and/or onium salts. The catalyst can be used as 1 to 55% strength by weight solution. The amount of the catalyst added can be 0.0001 mol to 0.1 mol, based on the total moles of the aromatic monohydroxy compound used.

Onium salts refer to compounds such as $NR_4X$, wherein the radicals R, independently of one another, can be H and/or an alkyl and/or aryl radical and X is an anion, such as, for example, chloride, bromide or iodide.

Specifically mentioned are nitrogenous catalysts, for example, tributylamine, triethylamine, and N-ethylpiperidine.

Optionally, an inert organic solvent can be present. Examples of solvents include aromatic solvents, halogenated, (specifically chlorinated), aliphatic or aromatic solvents, or combinations comprising at least one of the foregoing. These are, for example, toluene, dichloromethane, the various dichloroethane and chloropropane compounds, chlorobenzene and chlorotoluene or combinations comprising at least one of the foregoing. Dichloromethane is specifically mentioned.

Conditions for carrying out the reactions according to a phase boundary process have been described for example in U.S. Pat. Nos. 4,016,190, 8,518,231, EP 1219589, EP 1216981, EP 1216982 and EP 784048.

Optionally, the reaction of phosgene and the aromatic monohydroxy compound can be conducted in the presence of heterogeneous catalysts. Heterogeneous catalysts are known and have been described in EP 483632, U.S. Pat. Nos. 5,478,961, 5,239,105 and 5,136, 077.

A method of producing a dialkyl carbonate comprises reacting an alkyl monohydroxy compound with the phosgene. Phosgene can be used in the liquid state, gaseous state or in an inert solvent.

Alkyl monohydroxy compounds include all isomers of linear and branched $C_{1-12}$ aliphatic alcohols and $C_{4-8}$ cycloaliphatic alcohols, each of which can be unsubstituted or substituted with 1 to 3 halogen, $C_{1-6}$ alkoxy, cyano, $C_{1-6}$ alkoxycarbonyl, $C_{6-12}$ aryloxycarbonyl, $C_{1-6}$ acyloxy, or nitro groups, provided that the valence of any substituted carbon is not exceeded. Examples of alkanols include methanol, ethanol, 1-propanol, 2-propanol, allyl alcohol, 1-butanol, 2-butanol, 3-buten-1-ol, amyl alcohol, 1-hexanol, 2-hexanol, 3-hexanol, 1-heptanol, 2-heptanol, 3-heptanol, and 4-heptanol, cyclopentanol, cyclohexanol, cycloheptanol, cyclooctanol, 3-methylcyclopentanol, 3-ethylcyclopentanol, 3-methylcyclohexanol, 2-ethylcyclohexanol (isomers), 2,3-dimethylcyclohexanol, 1,3-diethylcyclohexanol, 3-phenylcyclohexanol, benzyl alcohol, 2-phenethyl alcohol, and 3-phenylpropanol. In a specific embodiment, the alkanol is methanol, ethanol, 1-propanol, 2-propanol, 1-butanol, 2-butanol, or 3-butanol. Methanol is specifically mentioned.

The reaction conditions are not particularly limited and are known to a person skilled in the art without undue experimentation.

If desired, the dialkyl carbonate can be converted to a diaryl carbonate. For example, a dialkyl carbonate can react with an aromatic monohydroxy compound such as those described herein including phenol in the presence of a transesterification catalyst, to produce an alkyl aryl carbonate (e.g., phenyl methyl carbonate ("PMC")) and an aliphatic monohydric alcohol (e.g., methanol). In the second step, two molecules of the alkyl aryl carbonate undergo a disproportionation reaction to produce one molecule of diaryl carbonate (e.g., DPC) and one molecule of the starting material dialkyl carbonate (e.g., DMC). Examples of the catalyst include alkali metals and alkaline earth metals such as lithium, sodium, potassium, magnesium, calcium, and barium; basic compounds of alkali metals and alkaline earth metals such as hydrides, hydroxides, alkoxides, aryloxides, and amides; basic compounds of alkali metals and alkaline earth metals such as carbonates, bicarbonates, and organic acid salts; tertiary amines such as triethylamine, tributylamine, trihexylamine, and benzyldiethylamine; nitrogen-containing heteroaromatic compounds such as N-alkylpyrroles, N-alkylindoles, oxazoles, N-alkylimidazoles, N-alkylpyrazoles, oxadiazoles, pyridines, quinolines, isoquinolines, acridines, phenanthrolines, pyrimidines, pyrazine, and triazines; cyclic amidines such as diazobicycloundecene (DBU) and diazobicyclononene (DBN); tin compounds such as tributylmethoxytin, dibutyldiethoxytin, dibutylphenoxytin, diphenylmethoxytin, dibutyltin acetate, tributyltin chloride, and tin 2-ethylhexanoate; zinc compounds such as dimethoxyzinc, diethoxyzinc, ethylenedioxyzinc, and dibutoxyzinc; aluminum compounds such as aluminum trimethoxide, aluminum triisopropoxide, and aluminum tributoxide; titanium compounds such as tetramethoxytitanium, tetraethoxytitanium, tetrabutoxytitanium, dichlorodimethoxytitanium, tetraisopropoxytitanium, titanium acetate, and titanium acetylacetonate; phosphorus compounds such as trimethylphosphine, triethylphosphine, tributylphosphine, triphenylphosphine, tributylmethylphosphonium halides, trioctylbutylphosphonium halides, and triphenylmethylphosphonium halides; zirconium compounds such as zirconium halides, zirconium acetylacetonate, zirconium alkoxides, and zirconium acetate; and lead and lead-containing compounds, for example lead oxides such as PbO, $PbO_2$, and $Pb_3O_4$, lead sulfides such as PbS, $Pb_2S_3$, and $PbS_2$, and lead hydroxides such as $Pb(OH)_2$, $Pb_3O_2(OH)_2$, $Pb_2[PbO_2(OH)_2]$, and $Pb_2O(OH)_2$. Specifically mentioned catalysts include titanium compounds such as titanium tetraphenoxide, titanium isopropylate, titanium tetrachloride, organotin compounds, and compounds of copper, lead, zinc, iron, and zirconium, and combinations comprising at least one of the foregoing. Specifically mentioned catalysts include titanium compounds such as titanium tetraphenoxide, titanium isopropylate, titanium tetrachloride, organotin compounds, and compounds of copper, lead, zinc, iron, and zirconium, and combinations comprising at least one of the foregoing.

In the polymerization of a polycarbonate, a dihydroxy compound can be used as a reactant with phosgene as a carbonate source. "Polycarbonate" as used herein means a homopolymer or copolymer having repeating structural carbonate units of formula (1)

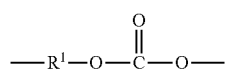

(1)

wherein at least 60 percent of the total number of $R^1$ groups are aromatic, or each $R^1$ contains at least one $C_{6-30}$ aromatic group. Specifically, each $R^1$ can be derived from a dihydroxy compound such as an aromatic dihydroxy compound of formula (2) or a bisphenol of formula (3).

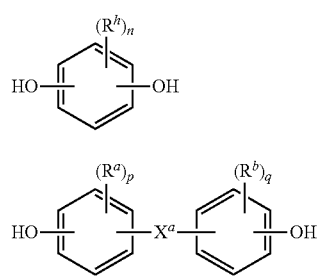

In formula (2), each $R^h$ is independently a halogen atom, for example bromine, a $C_{1-10}$ hydrocarbyl group such as a $C_{1-10}$ alkyl, a halogen-substituted $C_{1-10}$ alkyl, a $C_{6-10}$ aryl, or a halogen-substituted $C_{6-10}$ aryl, and n is 0 to 4.

In formula (3), $R^a$ and $R^b$ are each independently a halogen, $C_{1-12}$ alkoxy, or $C_{1-12}$ alkyl; and p and q are each independently integers of 0 to 4, such that when p or q is less than 4, the valence of each carbon of the ring is filled by hydrogen. In an embodiment, p and q is each 0, or p and q is each 1, and $R^a$ and $R^b$ are each a $C_{1-3}$ alkyl group, specifically methyl, disposed meta to the hydroxy group on each arylene group. $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group, for example, a single bond, —O—, —S—, —S(O)—, —S(O)$_2$—, —C(O)—, or a $C_{1-18}$ organic group, which can be cyclic or acyclic, aromatic or non-aromatic, and can further comprise heteroatoms such as halogens, oxygen, nitrogen, sulfur, silicon, or phosphorous. For example, $X^a$ can be a substituted or unsubstituted $C_{3-18}$ cycloalkylidene; a $C_{1-25}$ alkylidene of the formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl; or a group of the formula —C(=$R^e$)— wherein $R^e$ is a divalent $C_{1-12}$ hydrocarbon group.

Some illustrative examples of specific dihydroxy compounds include the following: bisphenol compounds such as 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis (hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl) sulfone, 9,9-bis (4-hydroxyphenyl)fluorine, 2,7-dihydroxypyrene, 6,6'-dihydroxy-3,3,3', 3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole; substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like.

Specific dihydroxy compounds include resorcinol, 2,2-bis (4-hydroxyphenyl) propane ("bisphenol A" or "BPA", in which each of $A^1$ and $A^2$ is p-phenylene and $Y^1$ is isopropylidene in formula (3)), 3,3-bis(4-hydroxyphenyl) phthalimidine, 2-phenyl-3,3'-bis(4-hydroxyphenyl) phthalimidine (also known as N-phenyl phenolphthalein bisphenol, "PPPBP", or 3,3-bis(4-hydroxyphenyl)-2-phenylisoindolin-1-one), 1,1-bis(4-hydroxy-3-methylphenyl)cyclohexane (DMBPC), and 1,1-bis(4-hydroxy-3-methylphenyl)-3,3,5-trimethylcyclohexane (isophorone bisphenol).

"Polycarbonates" as used herein include homopolycarbonates (wherein each $R^1$ in the polymer is the same), copolymers comprising different $R^1$ moieties in the carbonate ("copolycarbonates"), and copolymers comprising carbonate units and other types of polymer units, such as polysiloxane units, ester units, and the like.

The polycarbonate can be made by an interfacial polymerization process or in a melt polymerization process, which can be a continuous melt process. Although the reaction conditions for interfacial polymerization can vary, an exemplary process generally involves dissolving or dispersing a dihydric phenol reactant in aqueous NaOH or KOH, adding the resulting mixture to a water-immiscible solvent medium, and contacting the reactants with a carbonate precursor, for example, phosgene or a diaryl carbonate, in the presence of a catalyst such as, for example, a tertiary amine or a phase transfer catalyst, under controlled pH conditions, e.g., 8 to 10. The water immiscible solvent can be, for example, methylene chloride, ethylene dichloride, 1,2-dichloroethane, chlorobenzene, toluene, and the like.

Among tertiary amines that can be used in interfacial polymerization are aliphatic tertiary amines such as triethylamine and tributylamine, cycloaliphatic tertiary amines such as N,N-diethyl-cyclohexylamine, and aromatic tertiary amines such as N,N-dimethylaniline. Among the phase transfer catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Examples of phase transfer catalysts include $(CH_3(CH_2)_3)_4NX$, $(CH_3(CH_2)_3)_4PX$, $(CH_3(CH_2)_5)_4NX$, $(CH_3(CH_2)_6)_4NX$, $(CH_3(CH_2)_4)_4NX$, $CH_3(CH_3(CH_2)_3)_3NX$, and $CH_3(CH_3(CH_2)_2)_3NX$, wherein X is $Cl^-$, $Br^-$, a $C_{1-8}$ alkoxy group or a $C_{6-18}$ aryloxy group. An effective amount of a phase transfer catalyst can be 0.1 to 10 weight percent (wt %), or 0.5 to 2 wt %, each based on the weight of bisphenol in the phosgenation mixture.

Alternatively, melt processes can be used to make the polycarbonates. Generally, in the melt polymerization process, polycarbonates can be prepared by co-reacting, in a molten state, a dihydroxy reactant and a diaryl carbonate in the presence of a transesterification catalyst. The reaction can be carried out in typical polymerization equipment, such as a continuously stirred reactor (CSTR), plug flow reactor, wire wetting fall polymerizers, free fall polymerizers, wiped film polymerizers, BANBURY mixers, single or twin screw extruders, or a combination one or more of the foregoing. Volatile monohydric phenol is removed from the molten reactants by distillation and the polymer is isolated as a molten residue. Melt polymerization can be conducted as a batch process or as a continuous process. In either case, the melt polymerization conditions used can comprise two or more distinct reaction stages, for example, a first reaction stage in which the starting dihydroxy aromatic compound and diaryl carbonate are converted into an oligomeric polycarbonate and a second reaction stage wherein the oligomeric polycarbonate formed in the first reaction stage is converted to high molecular weight polycarbonate. Such "staged" polymerization reaction conditions are especially suitable for use in continuous polymerization systems wherein the starting monomers are oligomerized in a first reaction vessel and the oligomeric polycarbonate formed therein is continuously transferred to one or more downstream reactors in which the oligomeric polycarbonate is converted to high molecular weight polycarbonate. Typically, in the oligomerization stage the oligomeric polycarbonate produced has a number average molecular weight of 1,000 to 7,500 Daltons. In one or more subsequent polymerization stages the number average molecular weight (Mn) of the polycarbonate is increased to between 8,000 and 25,000 Daltons (using polycarbonate standard). Typically, solvents are not used in the process, and the reactants dihydroxy aromatic compound and the diaryl carbonate are in a molten state. The reaction temperature can be 100° C. to 350° C., specifically 180° C. to 310° C. The pressure can be at atmospheric pressure, supra-atmospheric pressure, or a range of pressures from atmospheric pressure to 15 ton in the initial stages of the reaction, and at a reduced pressure at later stages, for example, 0.2 to 15 torr. The reaction time is generally 0.1 hours to 10 hours.

Catalysts used in the melt transesterification polymerization production of polycarbonates can include one or both of a first catalyst comprising one or both of a phosphonium salt and an ammonium salt and an alkali catalyst comprising a source of one or both of alkali and alkaline earth ions. The first catalyst is typically volatile and degrades at elevated temperatures. The first catalyst is therefore preferred for use at early low-temperature polymerization stages. The alkali catalyst is typically more thermally stable and less volatile than the first catalyst.

The alkali catalyst can comprise a source of one or both of alkali or alkaline earth ions. The sources of these ions include alkali metal hydroxides such as lithium hydroxide, sodium hydroxide, and potassium hydroxide, as well as alkaline earth hydroxides such as magnesium hydroxide and calcium hydroxide. Other possible sources of alkali and alkaline earth metal ions include the corresponding salts of carboxylic acids (such as sodium acetate) and derivatives of ethylene diamine tetraacetic acid (EDTA) (such as EDTA tetrasodium salt, and EDTA magnesium disodium salt). Other alkali transesterification catalysts include alkali or alkaline earth metal salts of carbonate, such as $Cs_2CO_3$, $NaHCO_3$, $Na_2CO_3$, and the like, non-volatile inorganic acid such as $NaH_2PO_3$, $NaH_2PO_4$, $Na_2HPO_3$, $KH_2PO_4$, $CsH_2PO_4$, $Cs_2HPO_4$, and the like, or mixed salts of phosphoric acid, such as $NaKHPO_4$, $CsNaHPO_4$, $CsKHPO_4$, and the like. Combinations comprising at least one of any of the foregoing catalysts can be used.

Possible first catalysts can comprise a quaternary ammonium compound, a quaternary phosphonium compound, or a combination comprising at least one of the foregoing. The quaternary ammonium compound can be a compound of the structure $(R^4)_4N^+X^-$, wherein each $R^4$ is the same or different, and is a $C_{1-20}$ alkyl, a $C_{4-20}$ cycloalkyl, or a $C_{4-20}$ aryl; and $X^-$ is an organic or inorganic anion, for example, a hydroxide, halide, carboxylate, sulfonate, sulfate, formate, carbonate, or bicarbonate. Examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often used. The quaternary phosphonium compound can be a compound of the structure $(R^5)_4P^+X^-$, wherein each $R^5$ is the same or different, and is a $C_{1-20}$ alkyl, a $C_{4-20}$ cycloalkyl, or a $C_{4-20}$ aryl; and $X^-$ is an organic or inorganic anion, for example, a hydroxide, phenoxide, halide, carboxylate such as acetate or formate, sulfonate, sulfate, formate, carbonate, or bicarbonate. Where $X^-$ is a polyvalent anion such as carbonate or sulfate, it is understood that the positive and negative charges in the quaternary ammonium and phosphonium structures are properly balanced. For example, where $R^{20}$ to $R^{23}$ are each methyls and $X^-$ is carbonate, it is understood that $X^-$ represents $2(CO_3^{-2})$. Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often used.

The amount of first catalyst and alkali catalyst used can be based upon the total number of moles of dihydroxy compound used in the polymerization reaction. When referring to the ratio of first catalyst, for example, a phosphonium salt, to all dihydroxy compounds used in the polymerization reaction, it is convenient to refer to moles of phosphonium salt per mole of the dihydroxy compound, meaning the number of moles of phosphonium salt divided by the sum of the moles of each individual dihydroxy compound present in the reaction mixture. The alkali catalyst can be used in an amount sufficient to provide $1 \times 10^{-2}$ to $1 \times 10^{-8}$ moles, specifically, $1 \times 10^{-4}$ to $1 \times 10^{-7}$ moles of metal per mole of the dihydroxy compounds used. The amount of first catalyst (e.g., organic ammonium or phosphonium salts) can be $1 \times 10^{-2}$ to $1 \times 10^{-5}$, specifically $1 \times 10^{-3}$ to $1 \times 10^{-4}$ moles per total mole of the dihydroxy compounds in the reaction mixture.

Quenching of the transesterification catalysts and any reactive catalyst residues with an acidic compound after polymerization is completed can also be useful in some melt polymerization processes. Removal of catalyst residues and/or quenching agent and other volatile residues from the melt polymerization reaction after polymerization is completed can also be useful in some melt polymerization processes.

Set forth below are some embodiments of the method for making the phosgene, as well as apparatuses for use in the method.

In an embodiment, a method of producing phosgene in a tube reactor comprises: introducing a feed comprising carbon monoxide and chlorine to a tube of the reactor, the tube having a catalyst disposed therein, wherein the tube further comprises an internal scaffold, to produce a product composition comprising phosgene, and carbon tetrachloride in an amount of 0 to 10 ppm by volume based on the volume of the phosgene.

In specific embodiments of the foregoing process, one or more of the following conditions can apply: the internal scaffold comprises one or both of an internal insert and an internal fin; the internal insert, the internal fin, or both comprises an internal scaffolding element; the internal scaffolding element comprises a perpendicular element, an inner element, an angled element, or a combination comprising one or more of the foregoing; the catalyst is disposed on an inner wall of the tube; the catalyst is disposed in the tube as a packed bed; the catalyst varies in concentration, activity, or both from the feed end of the tube to the outlet end of the tube, wherein the variance is from low activity, concentration, or both at the inlet to relatively higher concentration, activity, or both, at the outlet; the variance is a smooth gradient; a peak temperature in the reactor is less than 800° C.; a peak temperature in the reactor is less than or equal to 400° C.; the reactor has a heat transfer area per unit volume of 250 to 10,000 m$^2$/m$^3$; or the reactor has a heat transfer area per unit volume of 500 to 10,000 m$^2$/m$^3$.

In an embodiment, a tube reactor comprises a shell and a tube located within the shell, with a cooling medium between the shell and the tube, wherein the tube further comprises an internal scaffold.

In specific embodiments of the foregoing reactor, one or more of the following conditions can apply: the internal scaffold comprises one or both of an internal insert and an internal fin; the internal insert, the internal fin, or both comprises an internal scaffolding element; the internal scaffolding element comprises a perpendicular element, an inner element, an angled element, or a combination comprising one or more of the foregoing; the catalyst is disposed on an inner wall of the tube; the catalyst is disposed in the tube as a packed bed; the catalyst varies in concentration, activity, or both from the feed end of the tube to the outlet end of the tube, wherein the variance is from low activity, concentration, or both at the inlet to relatively higher concentration, activity, or both, at the outlet; the variance is a smooth gradient; a peak temperature in the reactor is less than 800° C.; a peak temperature in the reactor is less than or equal to 400° C.; the reactor has a heat transfer area per unit volume of 250 to 10,000 m$^2$/m$^3$, or the reactor has a heat transfer area per unit volume of 500 to 10,000 m$^2$/m$^3$.

The following examples are provided to illustrate the present method. The examples are merely illustrative and are not intended to limit devices made in accordance with the disclosure to the materials, conditions, or process parameters set forth therein.

EXAMPLES

The Applicants surprisingly found that the heat removal rate varies inversely with the tube diameter and that the peak tube temperature increases with the increase in tube diameter, for example, from a lab scale operation performed in a tube with an outer diameter 0.5 to an industrial tube with an outer diameter of 2 inches. To quantify this relationship between peak tube temperature and the carbon tetrachloride formed in the synthesis of phosgene, a 1-D model was developed in Aspen custom modeler to show the effect of reactor dimensions on the process performance.

The reaction that is being modeled can be written as

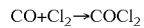

where the feed to the reactor comprise a mixture of CO and Cl$_2$ with a molar ratio of CO to Cl$_2$ of 1:1. A simple 1-D plug flow model was written for the material and energy conservation equations using the following:

The governing mass balance equations in non-dimensional form (1):

$$\frac{dN_i^*(x)}{dx^*} = \frac{\text{Rate}(x) \times \rho_b \times \pi \times R^2 \times L}{N_1(0) + N_2(0)} \tag{1}$$

$i = \text{CO, Cl}_2, \text{COCl}_2$

The non-dimensional energy balance across a plug in a reactor (2) and (3):

$$\dot{m}C_{p,g}\frac{dT^*(x)}{dx^*} = -U \times 2 \times \pi \times R \times T^* - \frac{\Delta H_R \times \text{Rate}(x) \times \rho_b \times \pi \times R^2 \times L}{(T_{ref} - T_c)} \tag{2}$$

$$\text{Rate} = KP_{CO}\left[\frac{P_{Cl_2}}{AP_{CO} + P_{COCl_2}}\right]^{0.25} \tag{3}$$

In order to improve the parameter estimation, Equations (1) and (2) were reformulated into a non-dimensional form. The kinetic equations in the non-dimensional form are (4), (5), and (6)

$$\log(K) = \frac{-k_{0mod}}{T_c + T^*(T_{ref} - T_c)} + k_1 \tag{4}$$

-continued $$\log(A) = \frac{-A_0}{T_c + T*(T_{ref} - T_c)} + A_1 \quad (5)$$

$$k_{0,mod} = \frac{k_0 f^{0.8} \left(\frac{P}{20}\right)^{0.125}}{\left(\frac{Q}{50}\right)^{0.15}} \quad (6)$$

wherein A is the reaction rate constant, $A_0$ is the kinetic parameter in rate equation, $A_1$ is the kinetic parameter in rate equation, $C_{p,g}$ is the specific heat capacity of gas (J/kg/K), f is the molar ratio of CO to $Cl_2$, K is the reaction rate constant, $k_0$ is the kinetic parameter in rate equation, $k_1$ is the kinetic parameter in rate equation, $k_{0mod}$ is the kinetic parameter in rate equation, L is the length of reactor (m), P is the pressure (psig), $N_i$ is the molar flow rate (mol/s), N* is the normalized molar flow rate ($N_i/N_{total}$) (where $N_{total}$ is the total molar flow rate), R is the internal radius (m), $T_c$ is the coolant/wall temperature and is assumed to be the same as the inlet feed temperature (i.e. $T_{in}=T_c$), $T_{in}$ is the inlet temperature (K), $T_{ref}$ is the reference temperature (K), T* is the normalized temperature $[(T-T_c)/(T_{ref}-T_c)]$ ($T_{ref}$ is a reference temperature which is sufficiently large and in the current simulation studies it has been assumed to be 700 K), U is the heat transfer coefficient (W/m²K), $\rho_b$ is the bulk density (Kg/m³), $\Delta H_R$ is the change in heat of reaction (Joules), Q is the volumetric flow rate (standard cubic meters per second), $N_1$ and $N_2$ are molar flow rates (moles per second), ṁ is mass flow rate (kilograms per second).

A set of experiments, Examples 1-9, was carried out in a reactor set up described in more detail by U.S. Pat. No. 6,399,823 in order to provide an estimation of the kinetic parameters and are shown in Table 1. $T_{exp}$ is the experimental temperature. SCCM is standard cubic centimeters per minute. In the examples, $\Delta H_R$ is −108,784 J/mol, U is 85.0 W/m2K, $T_{ref}$ is 700 K, $C_{p,g}$ is 659 J/kgK, and $\rho_b$ is 477 kg/m³.

TABLE 1

| Example | Q (SCCM) | $T_{in}$ (° C.) | $T_{exp}$ (° C.) |
|---|---|---|---|
| 1 | 100 | 80 | 113 |
| 2 | 100 | 100 | 144 |
| 3 | 250 | 100 | 171 |
| 4 | 150 | 120 | 198 |
| 5 | 50 | 160 | 185 |
| 6 | 250 | 220 | 306 |
| 7 | 175 | 220 | 286 |
| 8 | 250 | 160 | 270 |
| 9 | 250 | 300 | 378 |

Based on the data obtained from Examples 1-9 and the kinetic equations as described above, the kinetic parameters were estimated using a Newton's method based least square estimation procedure within the simulation tool Aspen custom modeler. The kinetic parameters determined are shown in Table 2 and the validation of the kinetic parameters is shown in Table 3, where the experimental temperature is compared to the model temperature, $T_{model}$, for volumetric flow rates of 100 and 175 SCCM.

TABLE 2

| $k_0$ | $k_1$ | $A_0$ | $A_1$ |
|---|---|---|---|
| 1648 | 1.786 | 10010 | 18.792 |

TABLE 3

| Q(SCCM) | $T_{in}$ (° C.) | $T_{exp}$ (° C.) | $T_{model}$ (° C.) | % Error |
|---|---|---|---|---|
| 100 | 300 | 344 | 342 | −0.6 |
| 175 | 300 | 359 | 360 | 0.33 |

After the initial validation studies between the experiments and the developed model for the lab scale, the model was employed to predict the results for a large scale industrial unit. The base case which has been considered for scale up corresponds to a flow rate of 250 SCCM at an inlet temperature of 300° C. and for a schedule 160, 0.5 inch outer diameter pipe. The linear velocity corresponding to the base case has been assumed for a larger 2 inch outer diameter pipe. The model was used to simulate the temperature profile for a 7 foot long reactor. A comparison of the temperature profiles is shown in FIG. 1, where the dashed line is the lab scale tube with an outer diameter of 0.5 inches and the solid line in the industrial scale tube with an outer diameter of 2 inches.

FIG. 1 shows that scale-up of the lab scale tube results in an unacceptable, almost 100% increase in temperature in near the beginning of the tube.

These experiments show that at the lab scale in the reactor set up described by U.S. Pat. No. 6,399,823 that $CCl_4$ production can be correlated to a peak temperature rise observed within the reactor and the following transfer function, Equation (7), was developed:

$$\ln(CCl_4[ppm])=0.0049*T_{peak}(K)-1.817 \quad (7)$$

Equation 7 predicts that the amount of carbon tetrachloride in the phosgene increases in an exponential manner as the peak temperature, $T_{peak}$, increases. Assuming a similar relation holds, the $CCl_4$ formation would increase by more than 300% with respect to the lab scale case when used in an industrial setting. In other words, the carbon tetrachloride in phosgene increases by more than four times the observed value at lab scale for a given set of operating conditions upon scale-up from a 0.5 inch outer diameter tube reactor to the 2 inch tube used commonly in industrial multi-tubular reactors. This model clearly establishes our assertion that the carbon tetrachloride in phosgene would go up several times upon scale-up unless fundamental design changes are made to reactor design to improve heat transfer in industrial scale multitubular reactors.

Further embodiments of the methods and reactors disclosed herein are set forth below.

Embodiment 1: A method of producing carbonate, comprising: reacting a feed comprising carbon monoxide and chlorine in a tube of a reactor to produce a product composition comprising phosgene, wherein the tube has a particulate catalyst contained therein, wherein a thermally conductive material separate from the tube contacts at least a portion of the particulate catalyst, and wherein carbon tetrachloride is present in the product composition in an amount of 0 to 10 ppm by volume based on the volume of the phosgene, wherein the reactor is capable of producing greater than or equal to 2,000 kilograms of the first product per hour; and reacting a monohydroxy compound with the phosgene to produce the carbonate.

Embodiment 2: The method of Embodiment 1 and reactor of Embodiment 28, wherein the thermally conductive material provides a thermally conductive path between the particulate catalyst and the tube.

Embodiment 3: The method of any of Embodiments 1-2, and reactor of Embodiment 28, comprising the thermally conductive material in the form of a coating disposed on at least a portion of an exterior surface of the particulate catalyst, or a portion of an exterior surface of agglomerates of the particulate catalyst, or both.

Embodiment 4: The method of Embodiment 3 and reactor of Embodiment 28, wherein the coating has a coating thickness of 0.001 to 1 micrometer.

Embodiment 5: The method of any of Embodiments 3-4 and reactor of Embodiment 28, wherein the coating is deposited by chemical vapor deposition, thermal spraying, dip coating, or powder coating.

Embodiment 6: The method of any one of Embodiments 1-5 and reactor of Embodiment 28, comprising the thermally conductive material in the form of a thermally conductive, 3-dimensional mesh.

Embodiment 7: The method of Embodiment 6 and reactor of Embodiment 28, wherein openings of the mesh have an average diameter larger than an average diameter of the particulate catalyst.

Embodiment 8: The method of any of Embodiments 1-7 and reactor of Embodiment 28, comprising the thermally conductive material in the form of a particulate material distributed within and in physical contact with the particulate catalyst.

Embodiment 9: The method of Embodiment 8 and reactor of Embodiment 28, wherein the particulate material and the particulate catalyst are in physical contact with a mesh disposed within the tube.

Embodiment 10: The method of Embodiment 9 and reactor of Embodiment 28, wherein openings of the mesh have an average diameter smaller than an average diameter of the particulate material.

Embodiment 11: The method of any one of Embodiments 1-10 and reactor of Embodiment 28, comprising the thermally conductive material in the form of a dopant in the particulate catalyst in an amount of greater than or equal to 10,000 ppm by weight of the particulate catalyst.

Embodiment 12: The method of Embodiment 11 and reactor of Embodiment 28, wherein the amount of dopant is greater than or equal to 100,000 ppm by weight of the particulate catalyst.

Embodiment 13: The method of any one of Embodiments 1-12 and reactor of Embodiment 28, wherein the thermally conductive material has a thermal conductivity of greater than 2 W/(m·K), greater than 15 W/(m·K), greater than 50 W/(m·K), or greater than 100 W/(m·K).

Embodiment 14: The method of Embodiment 13 and reactor of Embodiment 28, wherein the thermal conductivity is greater than 200 W/(m·K).

Embodiment 15: The method of any of Embodiments 1-14 and reactor of Embodiment 28, wherein the thermally conductive material is aluminum, aluminum brass, aluminum oxide, antimony, beryllium, beryllium oxide, brass, bronze, cadmium, carbon nanotubes, graphene, carbon steel, copper, gold, iridium, iron, lead, magnesium, molybdenum, nickel, silver, steel, stainless steel, Chrome Nickel Steel (18% Cr, 8% Ni), or a combination comprising at least one of the foregoing.

Embodiment 16: The method of any one of Embodiments 1-15 and reactor of Embodiment 28, wherein the catalyst varies in concentration, activity, or both from the feed end of the tube to the outlet end of the tube, wherein the variance is from low activity, concentration, or both at the inlet to relatively higher concentration, activity, or both, at the outlet.

Embodiment 17: The method of Embodiment 16 and reactor of Embodiment 28, wherein the variance is a smooth gradient.

Embodiment 18: The method of any one of Embodiments 1-17 and reactor of Embodiment 28, wherein a peak temperature in the reactor is less than 800° C.

Embodiment 19: The method of Embodiment 18 and reactor of Embodiment 28, wherein the peak temperature is less than or equal to 400° C.

Embodiment 20: The method of any one of Embodiments 1-19 and reactor of Embodiment 28, wherein the reactor has a heat transfer area per unit volume of 250 to 10,000 $m^2/m^3$.

Embodiment 21: The method of Embodiment 20, wherein the reactor has a heat transfer area per unit volume of 500 to 10,000 $m^2/m^3$.

Embodiment 22: The method of any of Embodiments 1-21, wherein the carbonate is dialkyl carbonate, and wherein the monohydroxy compound is an alkyl monohydroxy compound.

Embodiment 23: The method of Embodiment 22, wherein the dialkyl carbonate is dimethyl carbonate, and wherein the alkyl monohydroxy compound is methanol.

Embodiment 24: The method of any of Embodiments 22-23, further comprising reacting the dialkyl carbonate with an aromatic monohydroxy compound in the presence of a transesterification catalyst to produce an alkyl aryl carbonate; and converting the alkyl aryl carbonate in a disproportionation reaction to produce a diaryl carbonate.

Embodiment 25: The method of any of Embodiments 1-21, wherein the carbonate is diaryl carbonate, and wherein the monohydroxy compound is an aromatic monohydroxy compound.

Embodiment 26: The method of any of Embodiments 24-25, wherein the diaryl carbonate is diphenyl carbonate, and wherein the aromatic monohydroxy compound is phenol.

Embodiment 27: A method for making polycarbonate, comprising: polymerizing an aromatic dihydroxy compound with the diaryl carbonate of any of Embodiments 24-26.

Embodiment 28: A tube reactor comprising: a shell and a tube located within the shell, with a cooling medium between the shell and the tube; the tube having a particulate catalyst effective to convert carbon monoxide and chlorine to phosgene disposed therein; wherein a thermally conductive material separate from the tube contacts at least a portion of the particulate catalyst.

Embodiment 29: A method of using the reactor of Embodiment 28 in the method of any of Embodiments 1-27.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or" unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. In addition, it is to be understood that the described elements can be combined in any suitable manner in the various embodiments.

All references cited herein are incorporated herein by reference in their entirety.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

This application claims priority to European Patent Application 14382038 filed Feb. 4, 2014, the contents of which are herein incorporated in their entirety.

We claim:

1. A method of producing carbonate, comprising:
reacting a feed comprising carbon monoxide and chlorine in a tube of a reactor to produce a product composition comprising phosgene, wherein the tube has a particulate catalyst contained therein, wherein a thermally conductive material separate from the tube contacts at least a portion of the particulate catalyst, and wherein carbon tetrachloride is present in the product composition in an amount of 0 to 10 ppm by volume based on the volume of the phosgene, wherein the reactor is capable of producing greater than or equal to 2,000 kilograms of the product composition per hour; and
reacting a monohydroxy compound with the phosgene to produce the carbonate.

2. The method of claim 1, wherein the thermally conductive material provides a thermally conductive path between the particulate catalyst and the tube.

3. The method of claim 1, comprising the thermally conductive material in the form of a coating disposed on at least a portion of an exterior surface of the particulate catalyst, or a portion of an exterior surface of agglomerates of the particulate catalyst, or both.

4. The method of claim 1, comprising the thermally conductive material in the form of a thermally conductive, 3-dimensional mesh; and/or comprising the thermally conductive material in the form of a particulate material distributed within and in physical contact with the particulate catalyst.

5. The method of claim 4, wherein the thermally conductive material is in the form of the mesh and the particulate material and wherein the particulate material and the particulate catalyst are in physical contact with the mesh disposed within the tube.

6. The method of claim 1, comprising the thermally conductive material in the form of a dopant in the particulate catalyst in an amount of greater than or equal to 10,000 ppm by weight of the particulate catalyst.

7. The method of claim 1, wherein the thermally conductive material has a thermal conductivity of greater than 2 W/(m.K).

8. The method of claim 1 wherein the thermally conductive material is aluminum, aluminum brass, aluminum oxide, antimony, beryllium, beryllium oxide, brass, bronze, cadmium, carbon nanotubes, graphene, carbon steel, copper, gold, iridium, iron, lead, magnesium, molybdenum, nickel, silver, steel, stainless steel, chrome nickel steel (18% Cr, 8% Ni), or a combination comprising at least one of the foregoing.

9. The method of claim 1, wherein the catalyst varies in concentration, activity, or both from the feed end of the tube to the outlet end of the tube, wherein the variance is from low activity, concentration, or both at the inlet to relatively higher concentration, activity, or both, at the outlet; and optionally, wherein the variance is a smooth gradient.

10. The method of claim 1, wherein a peak temperature in the reactor is less than 800° C.; and/or wherein the reactor has a heat transfer area per unit volume of 250 to 10,000 $m^2/m^3$.

11. The method of claim 1, wherein the carbonate is dialkyl carbonate, and wherein the monohydroxy compound is an alkyl monohydroxy compound.

12. The method of claim 11, wherein the dialkyl carbonate is dimethyl carbonate, and wherein the alkyl monohydroxy compound is methanol.

13. The method of claim 11, further comprising reacting the dialkyl carbonate with an aromatic monohydroxy compound in the presence of a transesterification catalyst to produce an alkyl aryl carbonate; and converting the alkyl aryl carbonate in a disproportionation reaction to produce a diaryl carbonate.

14. The method of claim 1, wherein the carbonate is diaryl carbonate, and wherein the monohydroxy compound is an aromatic monohydroxy compound.

15. The method of claim 13, wherein the diaryl carbonate is diphenyl carbonate, and wherein the aromatic monohydroxy compound is phenol.

16. A method for making polycarbonate, comprising: polymerizing an aromatic dihydroxy compound with the diaryl carbonate of claim 14.

17. The method of claim 3, comprising the thermally conductive material in the form of the coating; wherein the coating has a coating thickness of 0.001 to 1 micrometers.

18. The method of claim 4, comprising the thermally conductive material in the form of the mesh; and wherein openings of the mesh have an average diameter larger than an average diameter of the particulate catalyst.

19. The method of claim 5, wherein openings of the mesh have an average diameter smaller than an average diameter of the particulate material.

20. The method of claim 10, wherein the peak temperature in the reactor is less than or equal to 400° C. and wherein the reactor has a heat transfer area per unit volume of 500 to 10,000 $m^2/m^3$.

* * * * *